United States Patent [19]

Wider et al.

[11] Patent Number: 5,184,618

[45] Date of Patent: Feb. 9, 1993

[54] BLOOD GAS PARAMETER MEASURING SYSTEM

[75] Inventors: Bernhard Wider, Oberjesingen; Michael Blank, Boeblingen; Joachim Vester, Aidlingen, all of Fed. Rep. of Germany

[73] Assignee: Hewlett Packard Company, Palo Alto, Calif.

[21] Appl. No.: 645,595

[22] Filed: Jan. 23, 1991

[30] Foreign Application Priority Data

Apr. 25, 1990 [EP] European Pat. Off. ........ 90107850.1

[51] Int. Cl.$^5$ .............................................. A61B 5/00
[52] U.S. Cl. ........................................ 128/634; 356/41
[58] Field of Search ............... 128/633, 634, 665, 666; 356/40, 41

[56] References Cited

U.S. PATENT DOCUMENTS

| 4,201,222 | 5/1980 | Hasse | 128/634 |
|---|---|---|---|
| 5,020,537 | 6/1991 | Günther | 128/634 |
| 5,120,510 | 6/1992 | Gourley et al. | 422/82.07 |
| 5,125,404 | 6/1992 | Kittrell et al. | 128/634 |
| 5,127,077 | 6/1992 | Iyer et al. | 385/116 |
| 5,127,405 | 7/1992 | Alcala et al. | 128/633 |

FOREIGN PATENT DOCUMENTS

| 0252578 | 1/1988 | European Pat. Off. |
| 0259951 | 3/1988 | European Pat. Off. |
| 0329297 | 8/1989 | European Pat. Off. |
| 0352631 | 1/1990 | European Pat. Off. |
| 0363219 | 4/1990 | European Pat. Off. |

Primary Examiner—Lee S. Cohen
Assistant Examiner—Kevin Pontius
Attorney, Agent, or Firm—Perman & Green

[57] ABSTRACT

A system for invasive measuring of blood gas parameters, such as pH, $pO_2$ or $pCO_2$, or for measuring other parameters influencing the time constant of the excited state of a fluorescent dye, comprises a light generation device including a generator (2), a delay device (4) and a light source (6), a fluorescent measuring probe (1), a light reception device (16), a light guide device, which is adapted to be switched over and which, in its first switching state, optically connects the light source (6) to the fluorescent measuring probe (1) and said probe (1) to the light reception device (16) and which, in its second switching state, establishes an optical connection between the light source (6) and the light reception device (16), a phase metering device (17 to 20, 23 to 27) as well as an evaluation device (28), which, in the second switching state of the light guide device (7), determines the transfer characteristic of the blood gas parameter measuring system and which, in the first switching state of the light guide device (7), determines the measuring value of the blood gas parameter on the basis of the transfer characteristic, the output signal of the phase metering device (17 to 20, 23 to 27) and a correlation between the respective values of the blood gas parameter and the associated values of the time constant of the fluorescent measuring probe (1), said correlation being predetermined for the fluorescent measuring probe (1).

14 Claims, 3 Drawing Sheets

BLOOD GAS PARAMETER MEASURING SYSTEM

DESCRIPTION

The present invention deals with a blood gas parameter measuring system for invasive measuring of blood gas parameters, such as PH, $pO_2$ or $pCO_2$, or for measuring other parameters influencing the time constant of the excited state of a fluorescent dye.

Such blood gas parameter measuring systems, which are known, for example, from the technical publication IEEE Transactions on Biomedical Engineering, Vol. BME-33, No. 2, February 1986, pages 117 to 132; J. L. Gehrich et al.: "Optical Fluorescence and Its Application to an Intravascular Blood Gas Monitoring System", essentially comprise a fluorescent measuring probe for invasive measurement of blood gas parameters, which is provided with a fluorescent dye in ion exchange connection with the blood. The fluorescent measuring probe is connected to a light source via a glass fibre, said light source being used for the purpose of supplying excitation light of a first wavelength to the dye within the fluorescent measuring probe. The molecules of the fluorescent dye are brought to an excited state by said light having the first wavelength. During the time that the molecules spend in the excited state, they lose part of the excitation energy initially supplied thereto. When the molecules then return to their ground energetic state, they will emit light of a second wavelength, which is longer than said first wavelength. Depending on the type of dye used, the time constant, which elapses between the excitation of the molecules of the dye by the excitation light supplied by the light source and the emission of the fluorescent light of the second wavelength, depends e.g. on the oxygen partial pressure $pO_2$ or on other blood gas parameters.

It follows that, in the case of the known blood gas parameter measuring system, the excitation light coming from the light source is supplied to the fluorescent measuring probe via an optical multiplexer, the fluorescent light of a second wavelength emitted by the fluorescent measuring probe is supplied to a light reception device via said optical multiplexer, and the output signal of said light reception device is supplied to a microprocessor after having been subjected to digital conversion. The optical multiplexer prevents light of the first wavelength from falling on the light reception device. The microprocessor measures the time constant of the amplitude decrease of the light having the second wavelength, which is emitted by the fluorescent measuring probe, and determines the oxygen partial pressure on the basis of said time constant.

It turned out that bends of the light guide glass fibre, which has connected thereto the fluorescent measuring probe, influence the amplitude of the received light having the second wavelength so that the changes in amplitude resulting from fibre bends cause corresponding mistakes in the determination of blood gas parameters in the case of the known blood gas parameter measuring system.

An additional problem of the known blood gas parameter measuring system is to be seen in the fact that any fluctuations of the transfer characteristic of the whole system will have a negative influence on the measuring accuracy. For example, a fluctuation of the measuring sensitivity of the light measuring device caused by temperature variations will cause a corresponding mistake in the determination of blood gas parameters.

Taking as a basis this prior art, the present invention is based on the task of providing a blood gas parameter measuring system for invasive measuring of blood gas parameters, which operates with increased measuring accuracy.

In accordance with a first solution concept of the present invention, the measuring system is provided with the following features:
(a) a light generation device including
  (a1) a generator,
  (a2) a controllable delay device and
  (a3) a light source connected to said delay device and used for producing excitation light of a first wavelength,
(b) a fluorescent measuring probe provided with
  (b1) a fluorescent dye in ion exchange connection with the blood,
  (b2) said fluorescent dye being adapted to be brought to an excited state by means of light of a first wavelength and returning, while emitting light of a second wavelength, from the excited state to a ground state with a time constant depending on the blood gas parameter to be measured,
(c) a light reception device by means of which light of said first and second wavelength can be converted into a reception signal,
(d) a light guide device, which is adapted to be switched over and which
  (d1) guides light of the first wavelength from the light source to the fluorescent measuring probe and light of the second wavelength from the fluorescent measuring probe to the light reception device in its first switching state, and
  (d2) guides light of the first wavelength from the light source to the light reception device in its second switching state,
(e) a phase metering device,
  (e1) which has supplied thereto a phase reference signal phaselocked to the output signal of the generator as well as the reception signal from the light reception device and
  (e2) which produces a phase metering signal indicative of the phase difference between these signals,
(f) an evaluation device,
  (f1) which has supplied thereto the phase metering signal and
  (f2) which, in the second switching state of the light guide device, determines the respective phase metering signal in the case of at least two control states of the delay device for determining the transfer characteristic of the blood gas parameter measuring system, and
  (f3) which, in the first switching state of the light guide device, determines the measuring value of the blood gas parameter on the basis of the transfer characteristic, the phase metering signal and a correlation between the respective values of the blood gas parameter and the associated values of the time constant, said correlation being predetermined for the fluorescent measuring probe.

The blood gas measuring system according to the present invention measures the phase shift between the light of a second wavelength emitted by the fluorescent measuring probe and the excitation light of a first wavelength. The system according to the invention carries out a self-calibration. For this purpose, the evaluation device determines the respective phase metering signal in the second switching state of the light guide device, in which the fluorescent measuring probe is optically bridged. On the basis of the phase metering signals, the transfer characteristic of the system is determined. Subsequently, the evaluation device switches the light guide device back into the first switching state. The actual measuring value of the blood gas parameter is now calculated on the basis of the determined transfer characteristic, the actual phase metering signal and the correlation between blood gas parameter values and associated time constants, said correlation being predetermined for the fluorescent probe.

It follows that the blood gas parameter measuring system according to the invention carries out a self-calibration in the case of which all the values of the transfer channel are taken into account. In contrast to amplitude measurement as a basis for the measurement of blood gas parameters, the blood gas parameter determination which is effected by means of phase metering and which is possible on the basis of said self-calibration is not influenced by glass fibre bends.

In accordance with a special aspect of the present invention, the phase metering device of the blood gas parameter measuring system according to the invention is provided with the following features:
  (e3) a first frequency dividing stage connected between the generator and the delay device and used for producing a control signal for the light source having a frequency which corresponds to the first wavelength,
  (e4) a second frequency dividing stage connected downstream of the generator and used for producing a signal having a second frequency,
  (e5) a first mixer, which has supplied thereto the control signal of said first frequency and the signal of said second frequency and which produces the phase reference signal having a third frequency which is low in comparison with said first and second frequencies,
  (e6) a second mixer connected downstream of the light reception device and used for mixing down the frequency of the reception signal by means of the signal having said second frequency, and
  (e7) a phase comparison circuit, which, on the basis of a phase comparison between the output signal of the second mixer and the phase reference signal, produces the phase metering signal indicative of the phase difference between these signals.

According to a further aspect of the present invention,
  (e5) the first mixer
  (e5.1) is a digital first mixer whose output signal is a square-wave signal, and
  (e7) the phase comparison circuit is provided with the following features:
  (e7.1) a first band-pass filter connected downstream of the second mixer and having a center frequency in the range of said third frequency,
  (e7.2) a comparator connected downstream of the band-pass filter and used for converting the band-pass filter output signal into a square-wave signal,
  (e7.3) an EXOR gate connected downstream of the comparator and the digital first mixer, and
  (e7.4) a second low-pass filter connected downstream of the EXOR gate and having a cut-off frequency below that of the first low-pass filter.

In accordance with an additional aspect of the present invention,
  (c) the light reception device is provided with the following features:
  (c1) an avalanche photodiode,
  (c2) a temperature sensor for measuring the temperature of the avalanche photodiode, and
  (c3) a power supply unit for producing a supply voltage for the avalanche photodiode in response to an output signal of the temperature sensor.

In accordance with a further aspect of the present invention,
  (d) the light guide device, which is adapted to be switched over, is provided with the following features:
  (d3) an optical switch associated with the light source and
  (d4) a second optical switch associated with the light reception device and adapted to be actuated together with said first optical switch.

According to an additional aspect of the present invention,
  (d) in the case of which the light guide device is provided with the following feature:
  (d5) an optical filter, which is arranged in the light path between the fluorescent measuring probe and the light reception device and which is of such a nature that, in the first switching state of the light guide device, light of the second wavelength can fall on the light reception device, whereas light of the first wavelength is prevented from falling on said device.

In accordance with another aspect of the invention, (a.2.1) said controllable delay device is connected between said generator and said light source.

According to an additional aspect of the invention, (a.2.2) said controllable delay device is connected between said light reception device and said phase metering device.

In the case of the first solution concept of the present invention, which has been described hereinbefore, it is necessary to use a light guide device which is adapted to be switched over and which can be defined by optical switches. In cases in which a light guide device of the switch-over type is not regarded as being desirable, the blood gas parameter measuring system according to the second solution concept of the present invention, which will be explained hereinbelow, can be used.

In accordance with the solution concept of the present invention, the blood gas parameter measuring system for invasive measuring of blood gas parameters is provided with the following features:
  (a) a first light source for producing excitation light of a first wavelength,
  (b) a second light source for producing excitation light of a second wavelength,
  (c) a fluorescent measuring probe provided with
  (c1) a fluorescent dye in ion exchange connection with the blood,
  (c2) said fluorescent dye being adapted to be brought to an excited state by means of light of a first wavelength and returning, while emitting light of a second wavelength, from the excited state to a ground state with a time constant depending on the blood gas parameter to be measured,
  (d) a first light reception device by means of which light of said second wavelength can be converted into a first reception signal, (e) a second light reception device by means of which light of said first and second wavelengths can be converted into a second reception signal, (f) a light guide device, (f1) which supplies light of the first wavelength from the first light source to the fluorescent measuring probe and to the second light reception device, and which supplies light of the second wavelength from the fluorescent measuring probe to the first light reception device and (f2) which supplies light of the second wavelength from said second light source to said first and second light reception devices, (g) a controllable delay device connected to one of the light reception devices, (h) a phase metering device, which is connected downstream of the delay device and the other light reception device and which produces a phase metering signal indicative of the phase difference between the signals supplied thereto, (i) an evaluation device, (i1) which has supplied thereto the phase metering signal, (i2) which, when the second light source is activated, determines the respective phase metering signal in the case of at least two control states of the delay device for determining the transfer characteristic of the blood gas parameter measuring system, and (i3) which, when the first light source is activated, determines the measuring value of the blood gas parameter on the basis of the transfer characteristic, the phase metering signal and a correlation between the respective values of the blood gas parameter and the associated values of the time constant, said correlation being predetermined for the fluorescent measuring probe.

Deviating from the blood gas parameter measuring system according to the first solution concept, the above-described blood gas parameter measuring system comprises, in addition to the first light source operating at the first wavelength, a second reference light source for producing excitation light of the second wavelength, which is used for calibration purposes alone. For the purpose of calibration or determination of the transfer characteristic of the blood gas parameter measuring system, the evaluation device of said system activates the second light source whose light is supplied to both light reception devices. Deviating from the system according to the first solution concept, the blood gas parameter measuring system according to the second solution concept has its controllable delay device connected downstream of one of the two light reception devices. When the second light source is activated, the delay device is controlled in two different control states so as to effect two different signal delays. This has the effect that the transfer characteristic of the blood gas parameter measuring system is determined while the fluorescent measuring probe is being bridged. Subsequently, the evaluation device deactivates the second light source and activates the first light source. On the basis of the measured phase metering signal in the deactivated state of the delay device, the actual blood gas parameter can be determined on the basis of the transfer characteristic, the instantaneous phase metering signal and a correlation between the respective values of the blood gas parameter and the associated time constants, said correlation being determined in advance for the fluorescent measuring probe used.

In accordance with a further aspect (f) the light guide device is provided with the following features:

(f3) first, second, third and fourth Y-shaped optical couplers, the first coupler having its only input connected to the first light source, the second coupler having its only input connected to the second light source, the third coupler having its only output connected to the first light reception device and the fourth coupler having its only output connected to the second light reception device, (f4) one output of said first coupler being connected to the fluorescent measuring probe, the other output of said first coupler being connected to one of the inputs of the fourth coupler, one output of the second coupler being connected to one of the outputs of the third coupler, the other output of the second coupler being connected to the other input of the fourth coupler and the fluorescent measuring probe being connected to the other input of the third coupler.

In accordance with an additional aspect of the present invention, (f) the light guide device is provided with (f4) a filter, which is arranged between the fluorescent measuring probe and the first light reception device and which permits light of the second wavelength to pass and to fall on the first light reception device, whereas it does not permit a passage of light of the first wavelength.

According to a further aspect of the present invention, (f) the light guide device is provided with (f5) an optical damping unit, which is arranged between the second light source and the second Y-shaped optical coupler and the damping ratio of which corresponds to the ratio between the light intensity of the excitation light for the fluorescent measuring probe and the light intensity of the fluorescent light emitted by said fluorescent measuring probe.

In accordance with an additional aspect of the invention, (h) the phase metering device is provided with the following features:

(h1) a first band-pass filter connected downstream of the first light reception device, (h2) a second band-pass filter connected downstream of the second light reception device, (h3) a first comparator connected downstream of the first band-pass filter, and (h4) a second comparator connected downstream of said second band-pass filter and having connected thereto the delay device.

According to a further aspect of the present invention, (h) the phase metering device is provided with the following features:

(h5) an EXOR gate connected downstream of the first band-pass filter and the delay device and (h6) a low-pass filter connected downstream of the EXOR gate.

Making reference to the drawings enclosed, two preferred embodiments of the blood gas parameter measuring system according to the present invention will be explained in detail hereinbelow. In the drawings.

Figure 1:
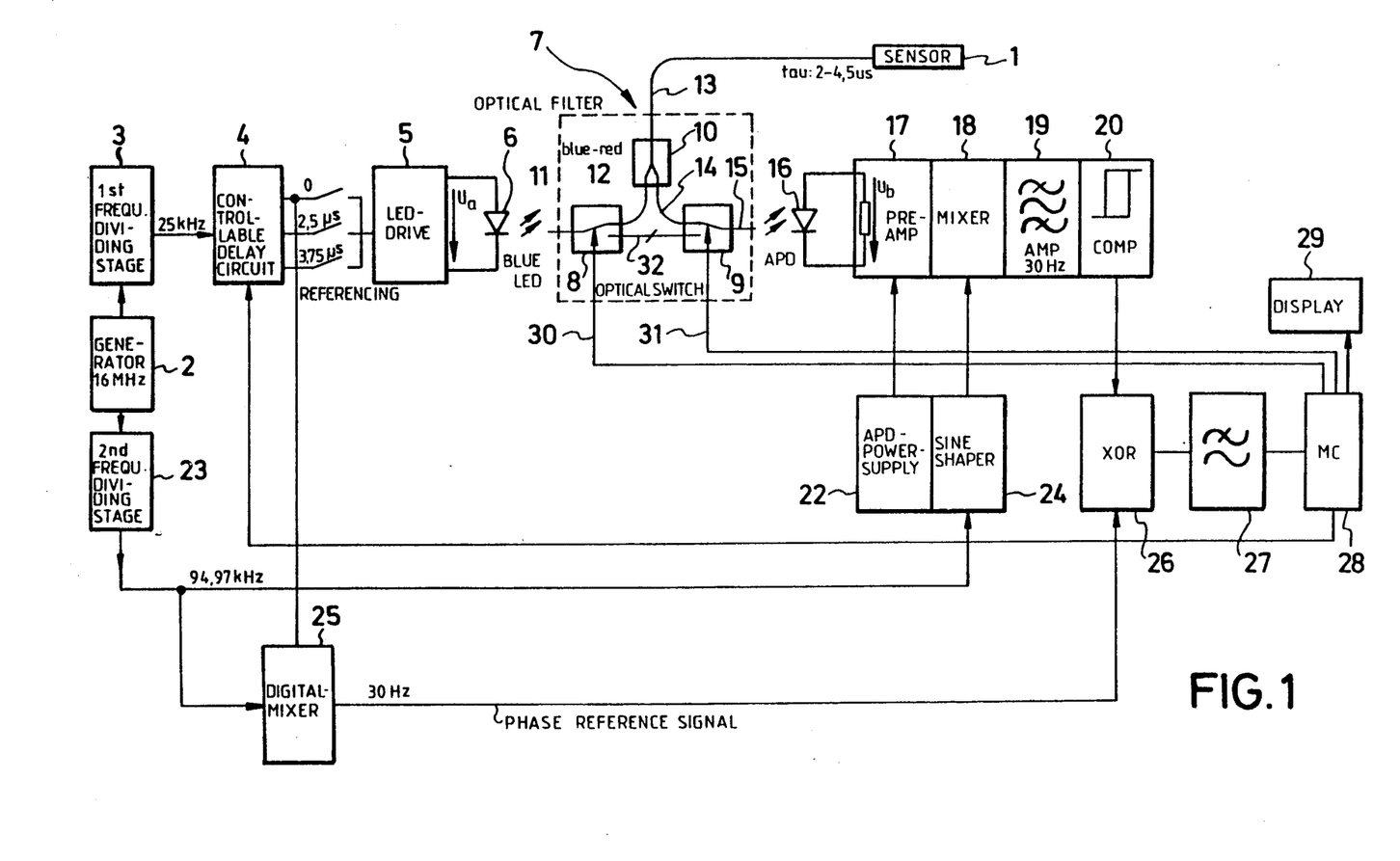
FIG. 1 shows a block diagram of an embodiment of the blood gas parameter measuring system according to the present invention in accordance with the first solution concept.

The blood gas parameter measuring system according to the first solution concept of the invention, which is shown in FIG. 1, comprises a fluorescent measuring probe 1 of the type known, in principle, from the prior art. Only by way of example, reference is made to European patent application EP-A1-0 336 985 and to European patent EP-B1-0 279 004, which are owned by the applicant, the disclosure of these prepublished publications being made the disclosure of the present application by making cross-reference to them.

Figure 2:
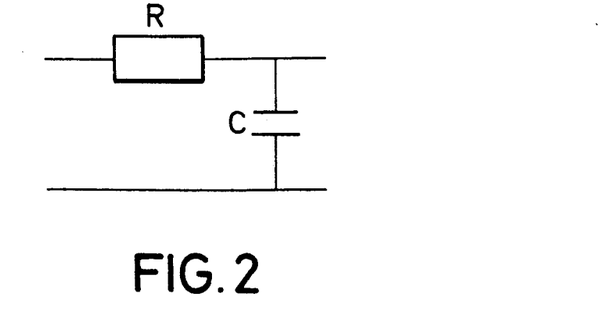
FIG. 2 shows an equivalent electric circuit diagram of a fluorescent measuring probe of the type used also in the case of the system according to FIG. 1.

As is, in principle, known, such a fluorescent measuring probe 1 comprises a cavity, which has provided therein a fluorescent dye, an ion exchange connection being established, via a semipermeable membrane, between said cavity and the blood to be examined. The fluorescent dye can be brought to an excited state by means of light of a first wavelength. As has been explained at the beginning, the excited molecules of the fluorescent dye return to their ground state, while emitting light of the second wavelength, with a time constant depending on the blood gas parameter to be measured. On the basis of this behavior, a fluorescent measuring probe 1 has associated therewith the equivalent electric circuit diagram of a low pass filter, which is shown in FIG. 2.

The blood gas parameter measuring system comprises a light generation device for exciting the dye of the fluorescent measuring probe 1 with light of a first wavelength, said light generation device comprising a 16 MHz generator 2, a first frequency dividing stage 3 connected downstream of said generator 2 and used for converting the 16 MHz signal into a 25 kHz signal, a controllable delay circuit connected downstream of said frequency dividing stage 3 and used for delaying the 25 kHz signal by 0 microseconds, 2.5 microseconds or 3.75 microseconds, an LED drive circuit 5 connected downstream of said delay circuit 4 as well as a blue LED 6 used for producing the excitation light of the first wavelength, which corresponds to the colour blue.

A light guide device, which is adapted to be switched over and which is, as a whole, provided with reference numeral 7, comprises first and second optical switches 8, 9 as well as an optical filter 10. In a first switching state of said first and second optical switches 8, 9, the excitation light of the first wavelength, which is emitted by the blue LED 6 and which is supplied to the first optical switch 8 via a glass fibre 11, is coupled into a second glass fibre 12, passed the optical filter 10 and is coupled into a third glass fibre 13, which has connected thereto the fluorescent measuring probe 1. After having been excited by the blue excitation light, said probe 1 emits a red light, which is supplied to the optical filter 10 via the third glass fibre 13, and via said optical filter 10 it is coupled into the fourth glass fibre 14, which is connected to the second optical switch 9. Via said second optical switch 9, the red light coming from the sensor 1 is coupled into a fifth glass fibre 15, said fifth glass fibre supplying said red light to an avalanche photodiode 16.

The optical filter 10, which can also be regarded as an optical multiplexer, prevents blue light (of the first wavelength) of the second glass fibre 12 from being coupled into the fourth glass fibre 14 so as to prevent an optical short circuit.

The avalanche photodiode 16 has connected downstream thereof a preamplifier 17, which is followed by a mixer 18. The output of the mixer 18 has connected thereto a first band-pass filter 19, which has a center frequency of 30 Hz and which is provided with an integrated amplifier stage, the output of said band-pass filter being connected to the input of a comparator 20, which converts the sinelike signal supplied thereto into a square-wave signal.

The 16 MHz generator 2 has connected thereto a second frequency dividing stage 23, which converts the 16 MHz signal supplied thereto into a 24.97 kHz signal, said 24.97 kHz signal being, on the one hand, supplied to a sine shaper 24 whose output is connected to the mixer 18 and being, on the other hand, supplied to one of the two inputs of a digital mixer 25. The second input of the digital mixer 25 is connected to the undelayed output of the controllable delay circuit 4. The digital mixer 25 produces on its output side a rectangular phase reference signal of 30 Hz.

The output of the digital mixer 25 and the output of the comparator 20 are connected to the two inputs of an EXOR gate whose output is connected to the input of a second low-pass filter 27, which has a cut-off frequency of 100 Hz and the output of which has, consequently, applied thereto a voltage $U_{out}$, said voltage being proportional to the phase shift between the output signal of the comparator 20 and the phase reference signal produced by the digital mixer 25.

The output of the second low-pass filter 27 is connected to the input of a microcontroller 28 (via an A-D converter which is not shown). A display output of the microcontroller 28 is connected to a display unit 29. The microcontroller 28 actuates the first and second optical switches 8, 9 via control lines 30, 31.

Via an additional control line 32, the microcontroller 28 actuates the controllable delay circuit 4 for the purpose of selecting a delay time of 0 microseconds, 2.5 microseconds or 3.75 microseconds.

Figure 4:
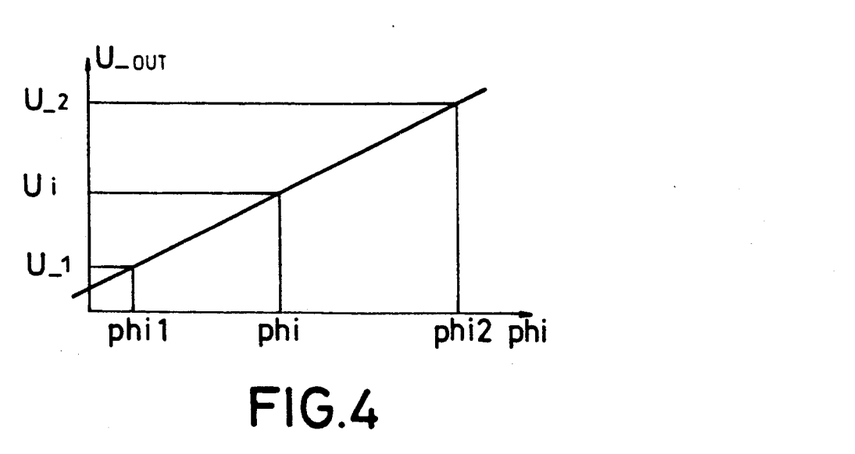
FIG. 4 shows a voltage phase diagram for explaining the determination of the characteristic of the system by an evaluation device of the system according to FIG. 1.

Before the microcontroller 28 switches the blood gas parameter measuring system to a measuring state, it switches said system to a calibration state for determining the transfer characteristic of the system. For this purpose, the two optical switches 8, 9 are actuated in such a way that light from the first glass fibre 11 is coupled into the fifth glass fibre 15 via the connecting glass fibre 32 so that it bypasses the fluorescent measuring probe 1 and is directly detected by the avalanche photodiode 16. In this state, the microcontroller 28 causes the controllable delay circuit 4 to delay the input signal by a first delay time of 2.5 microseconds or by a second delay time of 3.75 microseconds. These delays are indicated in FIG. 4 by the phase angles phi 1 and phi 2, respectively. A voltage $U_{out}$ at the output of the second low-pass filter 27 corresponds to each of said phases, said voltage points being indicated by U1, U2. On the basis of these measuring points, the microcontroller 28 determines the transfer characteristic of the whole system.

After having determined the transfer characteristic, the microcontroller 28 controls the controllable delay circuit 4 in such a way that said delay circuit permits passage of the input signal without delaying said signal. Furthermore, the microcontroller 28 switches the first and the second optical switches 8, 9 to the first switching state shown in FIG. 1.

Figure 3A:
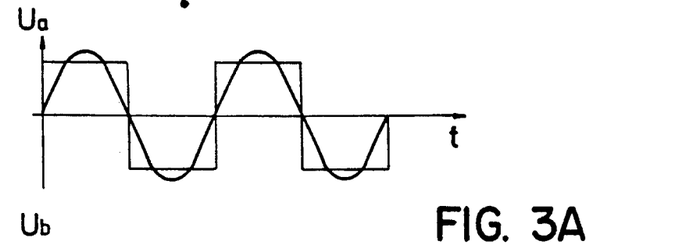
FIGS. 3a and 3b show the time curve of an input voltage for controlling a light source for exciting the fluorescent measuring probe as well as of the output voltage of a light reception device receiving the light emitted by the fluorescent measuring probe.

In this state, the sensor 1 is periodically acted upon by the blue excitation light, the excitation voltage of the blue LED 6 being provided with the reference symbol $U_a$ in FIG. 3a.

Figure 3B:
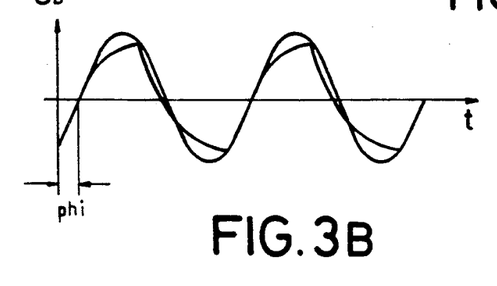

As has already been mentioned, a phase delay phi exists between the fluorescent red light, which is emitted by the sensor 1, and the blue excitation light, said phase delay phi being evident from the voltage curve $U_b$ which is shown in FIG. 3b and which is representative of the voltage across a high-value measuring resistor in the interior of the preamplifier 17.

As can be seen from FIG. 4, the microcontroller determines, by means of the transfer characteristic, the phase measuring value phi on the basis of the instantaneous output voltage $U_i$ of the low-pass filter 27, the blood gas parameter value being determined on the basis of said phase measuring value via a stored table or an algorithm indicating the correlation between blood gas parameters and time constants to the fluorescent measuring probe 1 used.

Figure 5:
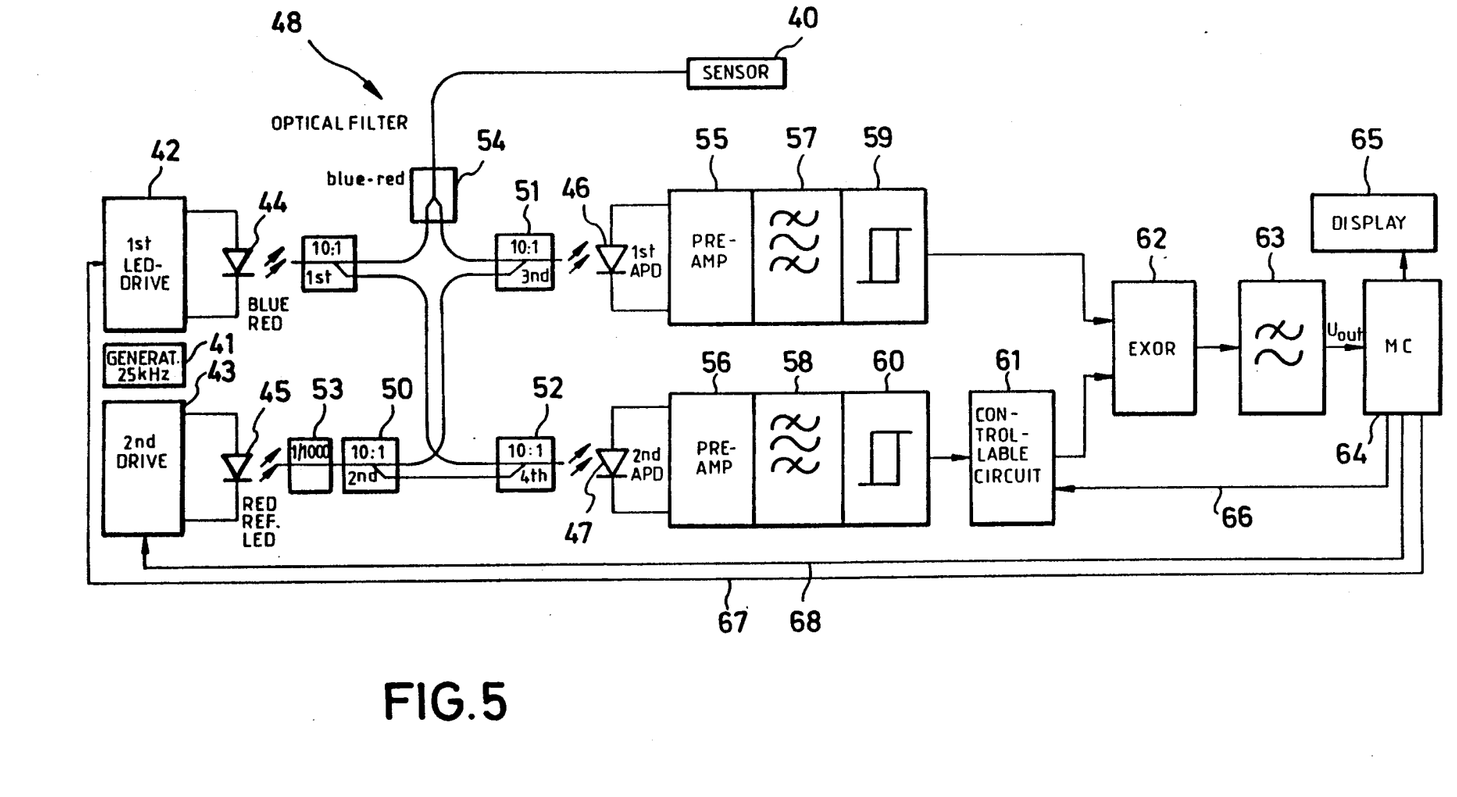
FIG. 5 shows a block diagram of an embodiment of the blood gas parameter measuring system according to the invention in accordance with the second solution concept.

The blood gas parameter measuring system according to the second solution concept of the invention, which is shown in FIG. 5, comprises a fluorescent measuring probe 40 corresponding to the above described fluorescent measuring probe 1 of the first embodiment.

A 25 kHz generator controls first and second LED drive circuits 42, 43.

The first LED drive circuit 42 has connected thereto a first, blue LED 44 for generating light of a first wavelength by means of which the fluorescent measuring probe 40 can be excited.

The second LED drive circuit 43 has connected thereto a second, red reference LED 45 for generating light of a second wavelength, said wavelength corresponding to the wavelength of the red fluorescent light emitted by the fluorescent measuring probe 40.

The system comprises first avalanche- and second PIN-photodiodes 46, 47. The two LEDs 44, 45, the fluorescent measuring probe 40 and the two photodiodes 46, 47 are optically connected by means of a light guide device, which is, as a whole, provided with reference numeral 48. The light guide device comprises first, second, third and fourth Y-shaped optical couplers 49, 50, 51, 52. The first coupler 49 has its input coupled to the blue LED 44. The second coupler 50 has its input coupled to the red reference LED 45 via a damping unit 53. The third coupler 51 has its output connected to the first avalanche photodiode 46, whereas the second coupler 52 has its output side connected to the second PIN-photodiode 47.

One output of the first coupler 49 is connected to the fluorescent measuring probe 40 via an optical filter 54. The other output of said coupler 49 is connected to an input of the fourth coupler 52. One output of the second coupler 50 is connected to one input of the third coupler 51, whereas the other output of said second coupler 50 is connected to the other input of the fourth coupler. The fluorescent measuring probe is connected to the other input of the third coupler 51 via the optical filter 54.

Hence, light from the blue LED 44 is supplied to the fluorescent measuring probe 40 and the second PIN-photodiode 47 via the light guide device 48.

Red light from the reference LED 45 is supplied to the first as well as to the second photodiode 46, 47 via said light guide device 48.

The two photodiodes 46, 47 are followed by preamplifiers 55, 56, which are, in turn, followed by a first band-pass filter 57 and a second band-pass filter 58, respectively, whose mid-frequency corresponds to the frequency of the generator 41. The band-pass filters 57, 58 are followed by first and second comparators 59, 60. The second comparator has connected thereto a controllable delay circuit 61. The output of the first comparator and that of the controllable delay circuit 61 are connected to the inputs of an EXOR gate 62, the output side of which is connected to a microcontroller 64 via a low-pass filter 63 having a cut-off frequency of 100 Hz. The microcontroller 64 is connected to a display means 65 its output side.

Via a first control line 66, the microcontroller 64 controls the selection of delay times of 0, 2.5 and 3.75 microseconds; these are the times by which the delay circuit 61 delays the signal supplied thereto. Via third and fourth control lines 67, 68, the microcontroller 64 activates either the first LED drive circuit 42 or the second LED drive circuit 43.

For determining the transfer characteristic of the system, the microcontroller 64 first activates the second LED drive circuit 43 so that both photodiodes 46, 47 have applied thereto light of the second wavelength in an equiphase mode. By an adequate delay caused by means of the delay circuit 61, the characteristic is determined in a manner corresponding to that of the first embodiment, and is then stored in the microcontroller 64.

Subsequently, the second LED drive circuit 43 is deactivated and the first LED drive circuit 42 is activated. The microcontroller determines the actual value of the blood gas parameter on the basis of the output voltage of the low-pass filter 63, the previously determined characteristic and a correlation between various values of the blood gas parameter and associated time constants, which was determined in advance for the fluorescent measuring probe used.

We claim:

1. A system for invasive measurement of blood gas parameters, including pH, $pO_2$ or $pCO_2$, or for measuring other parameters influencing the time constant of an excited state of a fluorescent dye, comprising:
  (a) a light generation device including
   (a1) a generator having an outer signal (2),
   (a2) a controllable delay device (4) having at least two delay states and
   (a3) a light source means (6) coupled to said generator (2) via said delay device (4) for producing excitation light of a first wavelength;
  (b) a fluorescent measuring probe (1) provided with
   (b1) a fluorescent dye that is positionable in ion exchange connection with blood;
   (b2) said fluorescent dye adapted to be brought to an excited state by means of light of a first wavelength and returning, while emitting light of a second wavelength, from the excited state to a ground state with a time constant depending on the blood gas parameter to be measured, (c) a light reception device (16) for converting light of said first and second wavelengths into a received signal;

(d) a switchable light guide means (7)

(d1) having at least two states and optically coupled between said light source (6); said light reception means (16) and said fluorescent measuring probe (1), for coupling, in a first switched state, light of the first wavelength from the light source (6) to the fluorescent measuring probe (1) and light of the second wavelength from the fluorescent measuring probe (1) to the light reception means (16), and (d2) for guiding light of the first wavelength from the light source means (6) to the light reception means (16) in a second switched state;

(e) a phase metering means (17 to 20, 23 to 27), coupled to said generator (2) and said light reception means (16)

(e1) for producing a phase reference signal phase-locked to the output signal of the generator (2) and responsive to the received signal from the light reception means (16), (e2) to produce a phase metering signal indicative of the phase difference between said output and receive signals;

(f) an evaluation means (28) connected to said phase metering means, (f1) and responsive to phase metering signals in the at least two delay states of said controllable delay device (4), when said switchable light guide means (7) is (f2) in the second switched state, for determining the transfer characteristic of the blood gas parameter measuring system, and (f3) which, in the first switched state of the light guide device (7), determines a value of the blood gas parameter on the basis of the transfer characteristic, the phase metering signal and a correlation between the respective values of the blood gas parameter and dependent values of said time constant, said correlation being predetermined for the fluorescent measuring probe (1).

2. A system according to claim 1, wherein the phase metering means (17 to 20, 23 to 27) comprises:

(e3) a first frequency dividing stage (3) connected between the generator (2) and the delay device (4) and used for producing a control signal for the light source means (6) and having a first frequency which corresponds to the first wavelength, (e4) a second frequency dividing stage (23) connected to the generator (2) and used for producing a signal having a second frequency, (e5) a first mixer means (25), which has supplied thereto the control signal of said first frequency and the signal of said second frequency and for producing the phase reference signal having a third frequency which is low in comparison with said first and second frequencies, (e6) a second mixer means (18) connected to said second frequency dividing stage (23) and to the light reception means (16) for mixing down the frequency of the received signal by means of the signal having said second frequency thus producing an output, and (e7) a phase comparison circuit means (26), responsive to a phase difference between the output signal of the second mixer means (18) and the phase reference signal, for producing the phase metering signal indicative of the phase difference between these signals.

3. A system according to claim 2, (e5) wherein the first mixer means produces an (e5.1) output signal that is a square-wave signal, and (e7) wherein the phase comparison circuit (26, 27) comprises:

(e7.1) a first band-pass filter (19) connected downstream of the second mixer (18) and having a center frequency in the range of said third frequency.

(e7.2) a comparator (20) connected downstream of the band-pass filter (19) and used for converting the band-pass filter output signal into a square-wave signal, (e7.3) an EXOR gate (26) connected downstream of the comparator (20) and the digital first mixer (25), and (e7.4) a low-pass filter (27) connected downstream of the EXOR gate (26) and having a cut-off frequency below that of the first band-pass filter (19).

4. A system according to claim 1, (c) wherein the light reception means comprises:

(c1) an avalanche photodiode (16), (c2) a temperature sensor means (21) for measuring the temperature of the avalanche photodiode (16), and (c3) a power supply means (22) connected to said temperature sensor (21) for producing a supply voltage for the avalanche photodiode (16) in response to an output signal of the temperature sensor means (21).

5. A system according to claim 1, (d) wherein the switchable light guide means (7) comprises:

(d3) an optical switch (8) coupled to the light source (6) and (d4) a second optical switch (9) coupled to the light reception device (16) and actuable in conjunction with said first optical switch (8).

6. A system according to claim 1, (d) wherein the light guide means (7) comprises:

(d5) an optical filter (10), arranged in the light path between the fluorescent measuring probe (1) and the light reception means (16) and which, in the first switched state of the light guide means (7), enables light of the second wavelength to reach light reception device (16), and prevents light of the first wavelength from reaching said light reception device (16).

7. A system according to claim 1, wherein (a2.1) said controllable delay device (4) is connected between said generator (2) and said light source means (6).

8. A system according to claim 1, wherein (a2.2) said controllable delay device (4) is connected between said light reception means (16) and said phase metering means (17 to 20, 23 to 27).

9. A system for invasive measuring of blood gas parameters, such as pH, $pO_2$, $pCO_2$, and other parameters influencing the time constant of the excited state of a fluorescent dye, comprising (a) a first light source means (44) for producing excitation light of a first wavelength;

(b) a second light source means (45) for producing excitation light of a second wavelength, (c) a fluorescent measuring probe (40) provided with (c1) a fluorescent dye positionable in ion exchange connection with blood, (c2) said fluorescent dye being adapted to be brought to an excited state by means of light of a first wavelength and returning, while emitting light of a second wavelength, from the excited state to a ground state with a time constant depending on the blood gas parameter to be measured;

(d) a first light reception means (46) for converting light of said second wavelength into a first reception signal;

(e) a second light reception means (47) for converting light of said first and second wavelengths into a second reception signal;

(f) a light guide means (48);

(f1) for coupling light of the first wavelength from the first light source means (44) to the fluorescent measuring probe (40) and to the second light reception means (47), and for coupling light of the second wavelength from the fluorescent measuring probe (40) to the first light reception device (46) and (f2) for further coupling light of the second wavelength from said second light source means (45) to said first and second light reception means (46, 47);

(g) a controllable delay device (61) connected to one of the light reception means (46, 47);

(h) a phase metering means (62, 63), which is connected downstream of the delay means (61) and the other light reception device (46), for producing a phase metering signal indicative of the phase difference between the reception signals supplied therefrom, (i) an evaluation means (64);

(i1) coupled to said phase metering means;

(i2) which, when the second light source means (45) is activated is responsive to respective phase metering signals that result during at least two control states of the delay device (61), for determining the transfer characteristic of the blood gas parameter measuring system, and (i3) when the first light source means (44) is activated, determining a value of the blood gas parameter on the basis of the transfer characteristic, the phase metering signal and a correlation between the respective values of the blood gas parameter and the dependent values of the time constant, said correlation being predetermined for the fluorescent measuring probe (40).

10. A system according to claim 9, (f) wherein the light guide means (48) comprises:

(f3) first, second, third and fourth Y-shaped optical coupler (49, 50, 51, 52), the first coupler having its only input connected to the first light source means (44), the second coupler having its only input connected to the second light source means (45), the third coupler having its only output connected to the first light reception means (46) and the fourth coupler having its only output connected to the second light reception means (47);

(f4) one output of said first coupler (49) being connected to the fluorescent measuring probe (40), the other output of said first coupler (49) being connected to one of the inputs of the fourth coupler (52).

one output of the second coupler (50) being connected to one of the outputs of the third coupler (51), the other output of the second coupler (50) being connected to the other input of the fourth coupler (52) and the fluorescent measuring probe (40) being connected to the other input of the third coupler (51).

11. A system according to claim 9, (f) wherein the light guide means (48) comprises:

(f4) a filter (54), which is arranged between the fluorescent measuring probe (40) and the first light reception means (46) and which permits light of the second wavelength to pass and to fall on the first light reception device (46), but does not permit a passage of light of the first wavelength.

12. A system according to claim 11, (f) wherein the light guide means (48) comprises:

(f5) an optical damping unit (53), which is arranged between the second light source means (45) and the second Y-shaped optical coupler (50), the damping ratio of which corresponds to the ratio between the light intensity of the excitation light for the fluorescent measuring probe (40) and the light intensity of the fluorescent light emitted by said fluorescent measuring probe.

13. A system according to claim 9, (h) wherein the phase metering means (62, 63) comprises:

(h1) a first band-pass filter (57) connected downstream of the first light reception means (46), (h2) a second band-pass filter (58) connected downstream of the second light reception means (47), (h3) a first comparator (59) connected downstream of the first band-pass filter (57), and (h4) a second comparator (60) connected downstream of said second band-pass filter (58) and having connected thereto the delay device (61).

14. A system according to any one of the claims 9 to 13, (h) wherein the phase metering means (62, 63) comprises:

(h5) an EXOR gate (62) connected downstream of the first band-pass filter (57) and the delay device (61) and (h6) a low-pass filter (63) connected downstream of the EXOR gate (62).

* * * * *

UNITED STATES PATENT AND TRADEMARK OFFICE
CERTIFICATE OF CORRECTION

PATENT NO. : 5,184,618

DATED : 02/09/93

INVENTOR(S) : Wider et al.

It is certified that error appears in the above-identified patent and that said Letters Patent is hereby corrected as shown below:

```
Column 10, line 57, the word "outer" should read --output--
Column 11, line 3, "," should read --;--
Column 11, line 4, "device" should read --means--
Column 11, line 12, after "source" insert --means--
Column 11, line 28, "receive" should read --received--
Column 11, line 36, after the word "state" insert --of the light guide
                    device (7)--
Column 11, line 59, after the word "frequency" take out the word "and"
Column 11, line 68, after the word "output" insert --signal--
Column 12, line 33, after the word "sensor" insert --means--
Column 12, line 60, the word "device" should read --means--
Column 13, line 40, after the word "activated" add --,--
Column 13, line 56, the word "coupler" should read --couplers--
Column 14, line 27, the word "device" should read --means--
```

Signed and Sealed this

Ninth Day of November, 1993

*Attest:*

BRUCE LEHMAN

*Attesting Officer*   *Commissioner of Patents and Trademarks*